United States Patent [19]

Abe et al.

[11] Patent Number: 5,482,733
[45] Date of Patent: Jan. 9, 1996

[54] METHOD FOR CONTROLLING AND/OR ELIMINATING HARMFUL LAWN GRASS INSECTS USING NON-POLLUTIVE SUBSTANCE

[75] Inventors: Toshiyuki Abe, Tokyo; Masayoshi Hatsukade, Shizuoka; Naomichi Nakashima, Tokyo, all of Japan

[73] Assignee: Hodogaya Chemical Co., Ltd., Tokyo, Japan

[21] Appl. No.: 283,551

[22] Filed: Aug. 1, 1994

[30] Foreign Application Priority Data

Aug. 2, 1993 [JP] Japan ................................ 5-208179

[51] Int. Cl.⁶ ............................ A01N 25/16; A01N 31/14
[52] U.S. Cl. ................ 427/4; 427/136; 427/155; 71/900
[58] Field of Search .................. 427/4, 136, 155; 47/2; 71/900

[56] References Cited

U.S. PATENT DOCUMENTS

| 2,875,555 | 3/1959 | Thiegs et al. ................... | 427/4 |
|---|---|---|---|
| 3,713,404 | 1/1973 | Lavo et al. ....................... | 71/900 |
| 3,891,571 | 6/1975 | Lambou et al. .................. | 427/4 |
| 4,190,428 | 2/1980 | Colton et al. ..................... | 71/900 |
| 4,299,839 | 11/1981 | Omura et al. .................... | 424/274 |
| 4,874,641 | 10/1989 | Kittle ................................ | 427/244 |
| 4,997,592 | 3/1991 | Woogerd .......................... | 71/900 |
| 5,066,428 | 11/1991 | Manlowe et al. ................. | 261/29 |
| 5,308,827 | 5/1994 | Sakamoto et al. ................ | 71/900 |

FOREIGN PATENT DOCUMENTS

| 3-81203 | 4/1991 | Japan . |
|---|---|---|
| 4-57296 | 9/1992 | Japan . |

*Primary Examiner*—Diana Dudash
*Attorney, Agent, or Firm*—Oblon, Spivak, McClelland, Maier & Neustadt

[57] ABSTRACT

A method for controlling and/or eliminating harmful lawn grass insects is disclosed, which comprises: foaming a surfactant composition having a total content of components present of from 0.2 to 50% by weight and comprising at least one surfactant selected from an anionic sulfonate, a higher fatty acid containing from 8 to 30 carbon atoms and salts of the higher fatty acid and a thickener; and applying the foam onto the surface of lawn grass in a thickness effective for controlling and/or eliminating the harmful lawn grass insects.

4 Claims, No Drawings

5,482,733

METHOD FOR CONTROLLING AND/OR ELIMINATING HARMFUL LAWN GRASS INSECTS USING NON-POLLUTIVE SUBSTANCE

FIELD OF THE INVENTION

The present invention relates to a method for controlling and/or eliminating harmful lawn grass insects using foam produced by foaming a non-pollutive and highly safe surfactant composition by means of a foaming machine and distributing it on lawn grass.

BACKGROUND OF THE INVENTION

Hithertofore, organic phosphoric and carbamate insecticides and so on are conventionally applied for harmful lawn grass insects. These insecticides involve problems such as an adverse effect on the environment due to their toxicities and the induction of resistance of the insects, their complicated procedures and harmness to the health of workers handling them. Particularly, with the recent demands for the reduction or non-use of agricultural chemicals on golf course turfs, the control and elimination of harmful lawn grass insects is becoming increasingly difficult. In addition, most of the major species of harmful lawn grass insects are nocturnal and thus their elimination is preferably conducted during their active period at night. However, no satisfactory method therefor has been found.

Accordingly, to solve such problems, a method has been demanded for controlling and eliminating insects with a good working efficiency, highly safety and non-pollution under a variety of complex conditions of location, climate and insect growth in various lawn areas.

On the other hand, an agricultural application of a stable, biodegradable foam using a solid surfactant has been proposed in JP-A-3-81203 (the term "JP-A" as used herein means "unexamined published Japanese Patent Application"). However, it mainly relates to the promotion of seed germination or field markers for the spraying of herbicides, pesticides, and the like. Further, a method in which agricultural chemicals such as insecticides and bactericides are sprayed in the form of foam has been proposed in JP-B-4-57296 (the term "JP-B" as used herein means "examined Japanese Patent Publication"). Thus, both methods only relate to the use of insecticides, bactericides and the like, and therefore they are simply variations of methods of distribution of agricultural chemicals.

SUMMARY OF THE INVENTION

Under these circumstances, the present inventors conducted extensive investigations on non-pollutive surfactant compositions and foaming methods therefor for use in the control and elimination of harmful lawn grass insects. The present invention has completed based on the above mentioned investigation.

Namely, an object of the present invention is to provide a method for controlling and/or eliminating harmful lawn grass insects which comprises:
foaming a surfactant composition having a total content of components present of from 0.2 to 50% by weight and comprising at least one surfactant selected from an anionic sulfonate, a higher fatty acid containing from 8 to 30 carbon atoms and salts of the higher fatty acid; and distributing the foam onto the surface of lawn grass in a thickness effective for controlling and/or eliminating the harmful lawn grass insects.

DETAILED DESCRIPTION OF THE INVENTION

The lawn areas to which the method of the present invention is applied include golf courses, lawn grass production sites, exercise facilities, racing turfs, parks, road shoulders, industrial development areas, housing development areas, and the like, and grassy areas similar thereto. These are places that are preferably treated for insect control and elimination at night when there is no influence on humans or animals. About 50 different types of lawn grass are planted, and there are many and diverse types of damage thereto due to the different ecological and feeding habits of various insects, but the method according to the present invention is not limited to any of these.

There are about 40 known species of harmful lawn grass insects, and these insects are distributed throughout the areas and locations which provide the best growing conditions for them. Also, there are many and various developmental ecologies. From the point of view of the classification of these harmful lawn grass insects, which are the subject of the present invention, there are 3 species of Orthoptera, 9 species of Hemiptera, 1 species of Hymenoptera, 2 species of Diptera, 8 species of Lepidoptera, and 16 species of Coleoptera, and important examples of them include *Gryllotalpa aflicana Palisot de Beauvois, Geoblissus hirlulus Burmeister, Antonins graminis Maskell, Spodoptera depravata Butler, Pediasia teterrellus Zincken, Agrotis ipsilon Hufnagel, Anomala octiescostata Burmeister, Hoplia communis Waterhause, Phyllopertha diversa Waterhouse, Melolontha japonica Burmeister, Adoretus tenuimaculatus Waterhouse, Anomala schonfeldti Ohause, Anomala asakana Sawada, Popillia japonica Newman, Anomala cuprea Hope, Sphenophorus venatus vestitus Chittenden,* and the like. Small animals other than insects include *Orthomorpha gracillis C.L. Koch, Armadillidium vulgate Latreille, Pheretima sp.* and the like. Most of these are nocturnal and only appear at night, and they are vigorously active, copulate and lay their eggs during a period of a few hours. During the daytime they disappear into the lawn soil or surrounding trees.

Therefore, according to the method of the present invention, the maximum effect is obtained by completing the distribution treatment before sundown when the harmful lawn grass insects begin to appear.

The surfactant composition according to the present invention comprises non-pollutive and biodegradable substances, has an excellent stability upon storage and dilution, and also good foamability.

Examples of the anionic sulfonate to be used in the present invention include sodium α-olefin sulfonate, sodium alkylbenzene sulfonate, calcium alkylbenzene sulfonate, sodium alkylsulfonate, sodium alkyl ether sulfonic ester, sodium phenyl ether sulfonic ester, sodium polyoxyethylene alkyl phenyl ether sulfonic ester, and the like.

Examples of the higher fatty acid of 8–30 carbon atoms to be used in the present invention include caprylic acid, capric acid, lauric acid, myristic acid, palmitic acid, stearic acid, oleic acid, behenic acid, coconut fatty acid, palm fatty acid, beef tallow fatty acid, and the like. Examples of the salt thereof include inorganic salts such as potassium salt, sodium salt, lithium salt, ammonium salt, salts with an ammonium substituted by 1 to 4 alkyl or hydroxyalkyl groups (e.g., triethanolamine, diethanolamine) and esters such as those with alcohols having 1 to 10 carbon atoms and with glycerol compounds.

Further, the surfactants disclosed in U.S. Pat. No. 4,874,641, which is hereby incorporated by reference, are also usable in the present invention.

Examples of the thickener to be used in the present invention include carboxymethyl cellulose and casein, polyvinyl alcohols, polyvinyl acridones and polyacrylic acids having a polymerization degree of from 1,000 to 4,000, sodium alginate, glues, starch, galactomannan, alkoxyamines, amines substituted by 1 to 3 hydroxyalkyl groups and the like. These thickener may be used either alone or in combination of two or more of them. The amount of the thickener to be added in the surfactant composition may be adjusted depending on the desired thickness and life of the foam, the lawn height, and the climactic conditions (weather, wind strength, temperature, etc.) at the time of distribution of the composition.

To the surfactant composition to be used in the present invention may also be added as necessary various types of non-pollutive additives such as sequestrants, pH buffers, fertilizers, attractants, perfumes and the like, so long as they do not adversely affect the surfactant composition.

The surfactant composition to be used in the present invention preferably has a pH value of 7 or more and a viscosity of 50 to 2,000 cps.

According to the method of the present invention, the surfactant composition may be used as such. Alternatively, a solution may be prepared in advance by mixing and dissolving the components of the surfactant composition and various additives in water at about 60° to 80° C. (hereunder referred to as a "concentrate"), and this concentrate is diluted at a 1–40 fold at use. In this instance, a concentrate of a higher concentration is advantageous in economical points of view since a concentrate of a lower content results in transport of a large quantity of product, almost of which is water, thereby causing undue expenses. Therefore, the concentrate is preferably prepared with a total content of the components of from 5 to 20% by weight, and is preferably diluted with water to 10–30 fold at use to give the surfactant composition having a total content of the components of 0.2 to 50% by weight. In general, the surfactant composition is foamed in an expansion ratio of 10 to 40 times by volume, preferably 10 to 30 times by volume.

The retention-time of the foam depends on the thickness of the foam, and also on the contents of the components and the expansion ratio. For example, foam with a high content of the components has a longer retention-time than foam with a low content of the components, assuming the foam thickness is the same. These conditions may be adjusted depending on the lawn conditions and species of insects being targeted at the site of distribution. Specifically, if the foam according to the present invention is to be distributed at about 2 hours prior to sundown, when the harmful lawn grass insects are the most active, and the foam is to completely disappear prior to the following sunrise, a favorable effect may be obtained by diluting a concentrate having a total content of the components of 5–10% by weight with water to 20–30 fold, foaming foam at an expansion ratio of 20 to 30-times by volume, and distributing the foam in a foam thickness of 0.3 mm to 5 cm, preferably 0.5 mm to 2 cm. The amount of the foam to be distributed here is generally from about 3 to 50 $l/m^2$, preferably from about 3 to 15 $l/m^2$.

In the practice of the present invention, foaming of the surfactant composition and the distribution of the foam can be made by means of, for example, a foaming machine described in JP-A-4-227039 (corresponding to U.S. Pat. No. 5,066,428, which is hereby incorporated by reference). Specifically, the surfactant composition is pumped into a foam block of the machine at a flow rate of 1 l/min. while injecting compressed air into the same foam block in an amount corresponding to a desired expansion ratio at a rate of 15–30 l/min. and the surfactant composition and the air are mixed with each other to give foam of the surfactant composition, which is then sprayed out from a nozzle via a hose to be distributed onto the lawn grass surface in a desired foam thickness in a conventional manner.

The present invention will now be explained in further detail with reference to the following Examples and Reference Examples.

PREPARATION EXAMPLE 1

| Component | Amount (% by weight) |
| --- | --- |
| Sodium α-olefin sulfonate $C_{10}$–$C_{12}$ | 3.85 |
| Stearic acid:palmitic acid (1:1) | 2.38 |
| Triethanolamine | 3.17 |
| Diethanolamine | 0.40 |
| Polyacrylic acid | 0.90 |
| Potassium polyphosphate | 1.00 |
| Water | 88.30 |

The above mentioned ingredients were combined, dissolved together at about 70° C., and reacted to obtain a concentrate of pH 7.7 and a viscosity of 180 cps.

This concentrate was diluted 25-fold with water, and foam was prepared with expansion ratios of 10, 20 and 30-times by volume.

PREPARATION EXAMPLE 2

| Component | Amount (% by weight) |
| --- | --- |
| Sodium α-olefin sulfonate $C_{10}$–$C_{12}$ | 3.85 |
| Stearic acid:palmitic acid (1:1) | 2.38 |
| Diethanolamine | 3.57 |
| Polyacrylic acid | 0.90 |
| Water | 89.30 |

The above mentioned ingredients were combined, dissolved together at about 70° C., and reacted to obtain a concentrate of pH 7.5 and a viscosity of 120 cps.

This concentrate was diluted 25-fold with water, and foam was prepared with expansion ratios of 10, 20 and 30-times by volume.

PREPARATION EXAMPLE 3

| Component | Amount (% by weight) |
| --- | --- |
| Sodium α-olefin sulfonate | 3.85 |

-continued

| Component | Amount (% by weight) |
|---|---|
| $C_{10}$–$C_{12}$ Stearic acid methyl ester:palmitic acid methyl ester (1:1) | 2.20 |
| Triethanolamine | 1.52 |
| Diethanolamine | 0.20 |
| Polyacrylic acid | 0.90 |
| Potassium polyphosphate | 1.00 |
| Water | 90.33 |

The above mentioned ingredients were combined, dissolved together at about 75° C., and reacted to obtain a concentrate of pH 7.9 and a viscosity of 140 cps.

This concentrate was diluted 25-fold with water, and foam was prepared with expansion ratios of 10, 20 and 30-times by volume.

As an example of harmful insect control and elimination, a treatment plot of a predetermined area was demarcated on a lawn area of a golf course having a number of harmful lawn grass insects.

EXAMPLE 1

Location:

Hamamatsu Seaside Golf Club (Iwata-shi, Shizuoka, Japan), NO. 16 course, the fairway and rough (Tifton turf)

Method:

Three test lawn zones each having an area of 64 m² (8 m×8 m) were provided (Zones A, B and C). The concentrate according to the present invention (Preparation Example 1) was foamed at an expansion ratio of 20-times by volume using the foaming machine described in U.S. Pat. No. 5,066,428, and the foam thus obtained was distributed for Zones A and C in a foam thickness of 4 cm and for Zone B in a foam thickness of 2 cm (hereunder referred to as "treated zones"). Untreated zones of the same areas were demarcated adjacent to each of these treated zones for comparison.

The distribution was started at 5:00 p.m. and ended at 6:00 pm., just prior to sundown when the gold beetle becomes active. The dead insects which had sunk into the foam in the treated zones were collected. Collection was made three times, at 7:20–9:00 p.m., 11:00–12:00 p.m., and 3:30–5:00 a.m.

In the untreated zones, as many insects as possible were collected between 7:20 and 9:00 p.m., by scooping them with a net of 30 cm in diameter.

The collected insects were placed in a 70% alcohol and carried back to determine the types and the numbers.

The results for Zone A are shown in Table 1, the results for Zone B in Table 2, and the results for Zone C in Table 3.

TABLE 1

(Control and Elimination Effects in Zone A (Location of Lawn: Rough; Foam Thickness: 4 cm))

| Kind of insect | Treated zone (number of dead insects) | Untreated zone (number of live insects) |
|---|---|---|
| *Pediasia teterrellus Zincken* | 50 | 15 |
| *Anomala asakana Sawada* | 38 | 24 |
| *Anomala schonfeldti Ohaus* | 29 | 9 |

TABLE 1-continued (Control and Elimination Effects in Zone A (Location of Lawn: Rough; Foam Thickness: 4 cm))

| Kind of insect | Treated zone (number of dead insects) | Untreated zone (number of live insects) |
|---|---|---|
| *Melolontha japonica Burmeister* | 29 | 4 |
| *Anomala cuprea Hope* | 1 | — |
| *Pheretima sp.* | 4 | — |
| Other | 1 | — |
| Total | 152 | 52 |

TABLE 2

(Control and Elimination Effects in Zone B (Location of Lawn: Fairway; Foam Thickness: 2 cm))

| Kind of insect | Treated zone (number of dead insects) | Untreated zone (number of live insects) |
|---|---|---|
| *Pediasia teterrellus Zincken* | 84 | 11 |
| *Anomala asakana Sawada* | 14 | 1 |
| *Anomala schonfeldti Ohaus* | 129 | 41 |
| *Melolontha japonica Burmeister* | 3 | — |
| *Pheretima sp.* | 3 | — |
| Other | 2 | — |
| Total | 235 | 53 |

TABLE 3

(Control and Elimination Effects in Zone C (Location of Lawn: Rough; Foam Thickness: 4 cm))

| Kind of insect | Treated zone (number of dead insects) | Untreated zone (number of live insects) |
|---|---|---|
| *Pediasia teterrellus Zincken* | 46 | 6 |
| *Anomala asakana Sawada* | 78 | 10 |
| *Anomala schonfeldti Ohaus* | 160 | — |
| *Melolontha japonica Burmeister* | 19 | — |
| *Pheretima sp.* | 4 | — |
| Fly | 7 | — |
| *Spodoptera teterrellus Zincken* (larva) | 2 | — |
| Other | 2 | — |
| Total | 235 | 53 |

The number of insects collected from the untreated zones was very small, whereas a large number of dead insects were collected from the treated zones. A surprising effect of the control and elimination of harmful lawn grass insects was observed.

No adverse effects of any kind such as damage from chemicals was observed on the lawn grass even after one month.

REFERENCE EXAMPLE 1

Location:

Hamamatsu Seaside Golf Club (Iwata-shi, Shizuoka, Japan), the green (Bento turf)

Method:

In the same manner as in Example 1, a test distribution was conducted for 2 zones of a lawn area of 25 m² (5 m×5 m) in foam thicknesses of 6–7 cm and 4 cm, respectively.

As a result, in the former case, the foam lasted 15 hours, while in the latter case the foam lasted 12 hours. In both of the treated zones, dead bodies of *Gryllotalpa aflicana Palisot de Beauvois* (8 bodies), *Anomala cuprea Hope* (15 bodies) and *Spodoptera depravata Butler* (larva: 3 bodies), which are recognized as difficult to eliminate with the conventional agricultural chemicals, were found within 1–2 hours after distribution of the foam. In addition, a number of dead bodies of Anomala species, *Ancylolomis japonica Zeller* and *Pediasia teterrellus Zincken* of around 1 cm in length were found, but they were all eaten by birds early the following morning.

No damage from the chemical to the Bento turf was found even 2 months after distribution.

REFERENCE EXAMPLE 2

The concentrate of Preparation Example 1 was diluted 25-fold with water, foams were prepared at expansion ratios of 10, 20 and 30-times by volume using the same foaming machine as in Example 1, the resulting foam was distributed onto the surface of wild lawn grass in foam thicknesses of 2 cm and 4 cm, respectively, and the difference in the retention time of the foams was observed. The results are shown in Table 4.

TABLE 4

| Expansion Ratio (times by volume) | Foam Thickness (cm) | Retention Time (hour) |
| --- | --- | --- |
| 10 | 4 | 22 |
| 10 | 2 | 14 |
| 20 | 4 | 12 |
| 20 | 2 | 7 |
| 30 | 4 | 5 |
| 30 | 2 | 3 |

REFERENCE EXAMPLE 3

The concentrates of Preparation Examples 2 and 3 were diluted 20-fold with water, foams were prepared at expansion ratios of 10, 20 and 30-times by volume using the same foaming machine as in Example 1, each of the foam was distributed onto the surface of wild lawn grass in a foam thickness 4 cm and the difference in the life of the foams was observed. The results are shown in Table 5.

TABLE 5

| | Retention Time (hour) | |
| --- | --- | --- |
| Expansion Ratio (times by volume) | Preparation Example 2 | Preparation Example 3 |
| 10 | 20 | 18 |
| 20 | 10 | 8 |
| 30 | 4 | 3 |

As is clear from the results shown in Tables 4 and 5 above, the life of the foam may be freely controlled by adjusting the expansion ratio and the foam thickness.

As mentioned above, the nearly complete control and elimination of harmful lawn grass insects whose elimination has hitherto been difficult with conventional agricultural chemicals and the like, has become attained by foaming a surfactant composition according to the present invention, and distributing and maintaining the foam at a desired foam thickness on the surface of a lawn. Furthermore, the method according to the present invention is excellent in that it is satisfactory non-pollutive means with no adverse effect on the environment, which has been demanded in recent years.

While the present invention has been described in detail and with reference to specific examples thereof, it will be apparent to one skilled in the art that various changes and modifications can be made therein without departing from the spirit and scope thereof.

What is claimed is:

1. A method for killing lawn grass insects which consists essentially of:

foaming an aqueous surfactant composition having a total content of active components present of from 0.2 to 50% by weight and consisting essentially of at least one surfactant selected from an anionic sulfonate, a higher fatty acid containing from 8 to 30 carbon atoms and a salt of the higher fatty acid; a thickener and optionally one or more non-polluting components selected from the group consisting of sequestrants, pH buffers, fertilizers, attractants and perfumes; and applying the foam onto the surface of lawn grass in a thickness of from 0.3 mm to 5 cm at a time within 2 hours prior to sundown, wherein said foam disappears prior to sunrise.

2. The method of claim 1, wherein said anionic sulfonate is selected from sodium α-olefin sulfonate, sodium alkylbenzene sulfonate, calcium alkylbenzene sulfonate, sodium alkylsulfonate, sodium alkyl ether sulfonic ester, sodium phenyl ether sulfonic ester and sodium polyoxyethylene alkyl phenyl ether sulfonic ester.

3. The method of claim 1, wherein said higher fatty acid is selected from caprylic acid, capric acid, lauric acid, myristic acid, palmitic acid, stearic acid, oleic acid, behenic acid, coconut fatty acid, palm fatty acid and beef tallow fatty acid.

4. The method of claim 1, wherein said salt is selected from potassium salt, sodium salt, lithium salt, ammonium salt, salts with an ammonium group substituted by 1 to 4 alkyl or hydroxyalkyl groups, esters with an alcohol having 1 to 10 carbon atoms and esters with a glycerol compound.

\* \* \* \* \*